(12) United States Patent
Gilliam et al.

(10) Patent No.: US 11,058,471 B2
(45) Date of Patent: *Jul. 13, 2021

(54) SCREW DRIVER SYSTEM (71) Applicants: b-ONE Ortho, Corp., Cedar Knolls, NJ (US); b-ONE Medical Biotech Corporation, Shanghai (CN)

(72) Inventors: Daniel S. Gilliam, Mission Viejo, CA (US); Bassam Masri, Vancouver (CA)

(73) Assignee: B-ONE MEDICAL BIOTECH CORPORATION, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/181,299

(22) Filed: Feb. 22, 2021

(65) Prior Publication Data

US 2021/0169542 A1   Jun. 10, 2021

Related U.S. Application Data

(60) Division of application No. 17/019,463, filed on Sep. 14, 2020, now Pat. No. 10,939,946, which is a continuation of application No. 15/982,270, filed on May 17, 2018, now Pat. No. 10,842,546.

(51) Int. Cl.
| | |
|---|---|
| *A61B 17/88* | (2006.01) |
| *B25B 23/00* | (2006.01) |
| *A61B 90/57* | (2016.01) |
| *A61B 17/28* | (2006.01) |
| *B25B 15/00* | (2006.01) |

(52) U.S. Cl.
CPC .......... *A61B 17/8877* (2013.01); *A61B 90/57* (2016.02); *B25B 23/0028* (2013.01); *B25B 23/0035* (2013.01); *A61B 17/28* (2013.01); *B25B 15/004* (2013.01)

(58) Field of Classification Search
None
See application file for complete search history.

(56) References Cited

U.S. PATENT DOCUMENTS

| | | | | |
|---|---|---|---|---|
| 2,387,928 | A * | 10/1945 | Monnier | ................ H01R 43/00 81/426.5 |
| 5,188,189 | A | 2/1993 | Hummel | |
| 5,391,181 | A * | 2/1995 | Johnson | ............... A61B 17/282 606/207 |

(Continued)

*Primary Examiner* — Brian D Keller
(74) *Attorney, Agent, or Firm* — Duane Morris LLP (57) ABSTRACT

Provided are a screw driver system and a screw driving bit. The screw driving bit includes a body having a first end and a second end with a longitudinal axis defined therebetween and an outer surface between the first and second ends. The screw driving bit includes a first circumferential groove and a second circumferential groove that are affixed in coaxially positioned arrangement about the longitudinal axis on the outer surface of the body each having a bottom surface. The bottom surface of the first circumferential groove defines a first outer diameter that is larger than a second outer diameter defined by the second circumferential groove. The guide clamp includes a jaw for holding the screw driving bit. When engaged with the first circumferential groove, the guide clamp prevents rotation of the screw driving bit. When engaged with the second circumferential groove, the guide clamp does not prevent rotation of the screw driving bit.

7 Claims, 8 Drawing Sheets

(56) References Cited

U.S. PATENT DOCUMENTS

| | | |
|---|---|---|
| 5,772,670 A | 6/1998 | Brosa |
| 5,922,008 A | 7/1999 | Gimpelson |
| 8,460,307 B2 | 6/2013 | Saidha et al. |
| 9,113,969 B2 * | 8/2015 | Niederberger ..... A61B 17/8019 |
| 2008/0177297 A1 | 7/2008 | Steiner et al. |
| 2013/0096568 A1 | 4/2013 | Justis |
| 2018/0368902 A1 | 12/2018 | Milor et al. |

* cited by examiner

SCREW DRIVER SYSTEM

CROSS-REFERENCE TO RELATED APPLICATIONS

This application is a divisional application of a co-pending U.S. patent application Ser. No. 17/019,463, filed on Mar. 9, 2021, which is a continuation of U.S. patent application Ser. No. 15/982,270, filed on May 17, 2018, the entire contents of which are incorporated herein by reference.

FIELD

The application relates to screw driver systems for use in surgical procedures.

BACKGROUND

Hip implant devices are a common means of replacing degenerated joints. Such implant devices often include a cup to replace or supplement the acetabulum. Often the acetabular cup includes a shell that is fixedly coupled to the patient's anatomy and a liner that fits within the shell and provides a smooth, resilient surface for contact with the head of a femoral implant. The shell can be fixed to the patient's anatomy using a variety of means, including screws. A variety of tools can be used to install and/or remove the screws into the cup including various screw drivers or wrenches.

SUMMARY

In one embodiment, a screw driving bit is disclosed that includes a body, a shaft engaging portion, a screw engaging portion, a first circumferential groove, and a second circumferential groove. The body has a first end and a second end and defines a longitudinal axis between the first end and the second end. The body has an outer surface with a cylindrical portion between the first end and the second end. The shaft engaging portion is at the first end and is configured to couple to a shaft. The screw engaging portion is at the second end and is shaped and configured to engage a head of a screw. The first circumferential groove and second circumferential groove are provided on the outer surface of the cylindrical portion. Each of the circumferential grooves has side walls and a bottom surface. The bottom surface of the first circumferential groove defines a first outer diameter and the bottom surface of the second circumferential groove defines a second outer diameter. The second circumferential groove is deeper than the first circumferential groove, whereby the second outer diameter is smaller than the first outer diameter. The first circumferential groove accommodates a guide clamp for tightly holding the screw driving bit by clamping the first circumferential groove's bottom surface. In addition, the second circumferential groove accommodates the guide clamp for rotatably holding the screw driving bit by engaging the second circumferential groove without clamping the second circumferential groove's bottom surface.

In another embodiment, a screw driver is disclosed that includes a shaft and a screw driving bit. The shaft is configured for manipulation by a user. The driving bit is configured to couple to the shaft. The driving bit includes a body, a shaft engaging portion, a screw engaging portion, a first circumferential groove and a second circumferential groove. The body has a first end and a second end and a longitudinal axis defined between the first end and the second end. The body has an outer surface with a cylindrical portion between the first end and the second end. The shaft engaging portion is at the first end and is configured to couple to the shaft. The screw engaging portion is at the second end and is shaped and configured to engage a head of a screw. The first circumferential groove and second circumferential groove are provided on the outer surface of the cylindrical portion. Each of the circumferential grooves has side walls and a bottom surface. The bottom surface of the first circumferential groove defines a first outer diameter and the bottom surface of the second circumferential groove defines a second outer diameter. The second circumferential groove is deeper than the first circumferential groove, whereby the second outer diameter is smaller than the first outer diameter. The first circumferential groove accommodates a guide clamp for tightly holding the screw driving bit by clamping the first circumferential groove's bottom surface. In addition, the second circumferential groove accommodates the guide clamp for rotatably holding the screw driving bit by engaging the second circumferential groove without clamping the second circumferential groove's bottom surface.

In another embodiment described herein, a screw driver system includes the screw driver and the guide clamp. The guide clamp includes an elongated shaft and a closable jaw. The closable jaw is configured for holding the screw driving bit. The jaw maintains an opening when closed, wherein the opening has a diameter that is larger than the second outer diameter of the screw driving bit but smaller than the first outer diameter of the screw driving bit. The guide clamp can tightly hold the screw driving bit by engaging the closable jaw into the first circumferential groove and clamping the first circumferential groove's bottom surface and restricting the screw driving bit from rotating about its longitudinal axis. The guide clamp can rotatably hold the screw driving bit by engaging the closable jaw into the second circumferential groove without clamping the second circumferential groove's bottom surface, thus allowing the screw driving bit to rotate about its longitudinal axis while being held by the guide clamp.

BRIEF DESCRIPTION OF THE DRAWINGS

These and other features and advantages of the screw driver systems described herein will be more fully disclosed in, or rendered obvious by, the following detailed description of the preferred embodiments, which is to be considered together with the accompanying drawings wherein like numbers refer to like parts and further wherein.

DETAILED DESCRIPTION

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively or operably connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

The present disclosure describes a screw driver system that simplifies the installation and/or removal of screws. Specifically, the screw driver systems described herein allow a surgeon or other operator to control a screw driving bit while installing or removing screws in an acetabular cup. Because of space constraints, when performing a hip replacement surgery, the surgeon is typically unable to manipulate the screw driving bit directly with her hand. As a result, the screw driving bit can disengage from the head of the screw. The screw driver systems described herein provide grooves that the surgeon can engage with a guide clamp to control and maneuver the screw driving bit during installation or removal of the screws. This greatly simplifies the installation or removal process.

Figure 1:
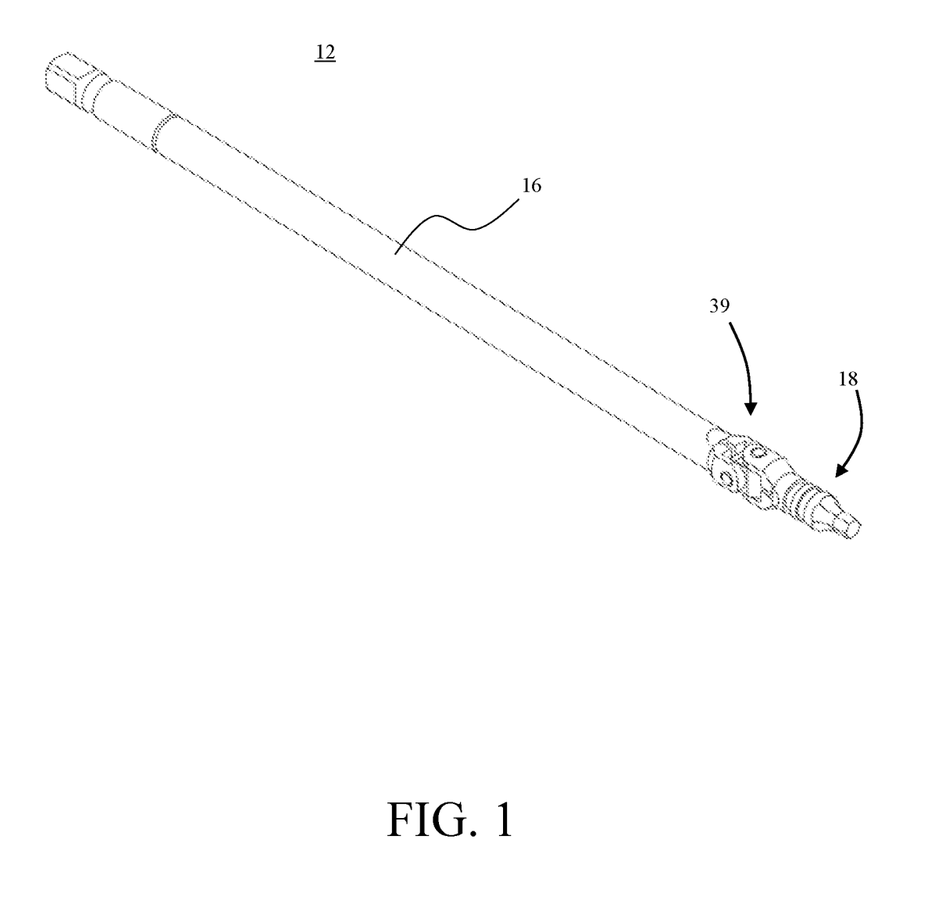
FIG. 1 shows a perspective view of a screw driver having an elongated shaft and a driving bit.

FIG. 1 shows a screw driver 12 comprising an elongated shaft 16 and a screw driving bit 18 according to one embodiment The elongated shaft 16 can be connected to a handle that is configured for manipulation by a user, such as a surgeon. In one embodiment, a universal joint 39 connects the screw driving bit 18 to the shaft 16. The universal joint 39 allows the shaft 16 and the screw driving bit 18 to articulate relative to one another to provide easier positioning of the driving bit 18 in a desired position.

Figure 2:
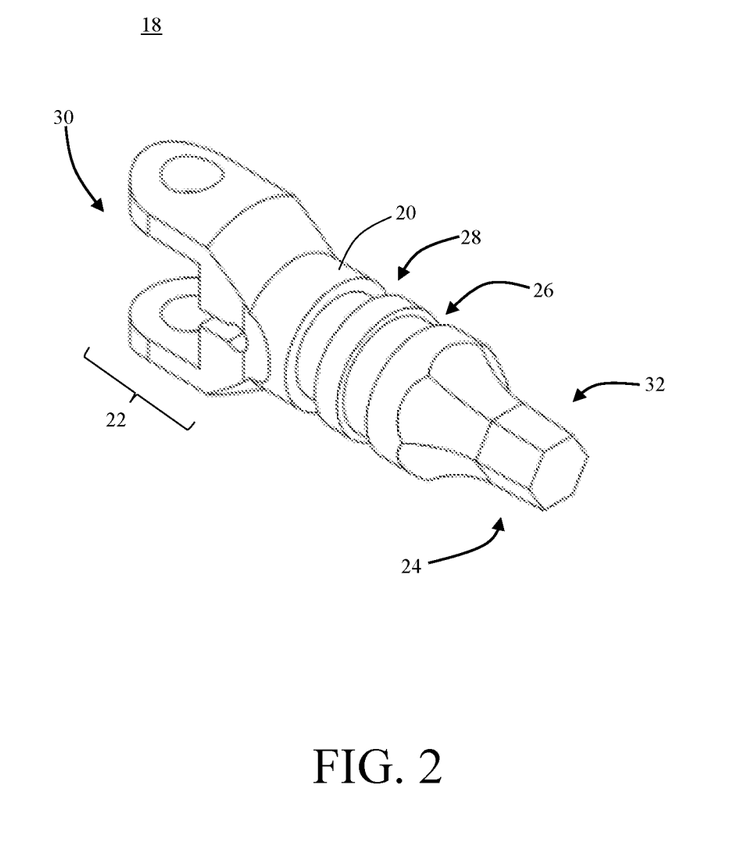
FIG. 2 shows a perspective view of a driving bit according to an embodiment of the present disclosure.
Figure 3A:
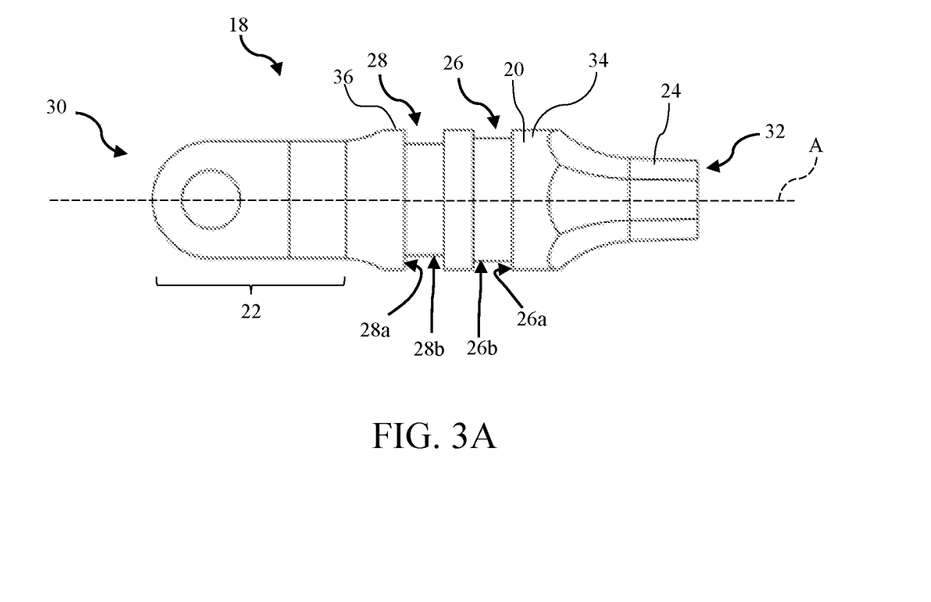
FIG. 3A shows a side view of the driving bit of FIG. 2.

As shown in FIGS. 2 and 3A, the screw driving bit 18 includes a body 20, a shaft engaging portion 22, a screw engaging portion 24, a first circumferential groove 26, and a second circumferential groove 28. The body 20 has a first end 30 and a second end 32 and defines a longitudinal axis A (shown in FIG. 3A) between the first end 30 and the second end 32. The body 20 has an outer surface 34 comprising a cylindrical portion 36 between the first end 30 and the second end 32.

Figure 3B:
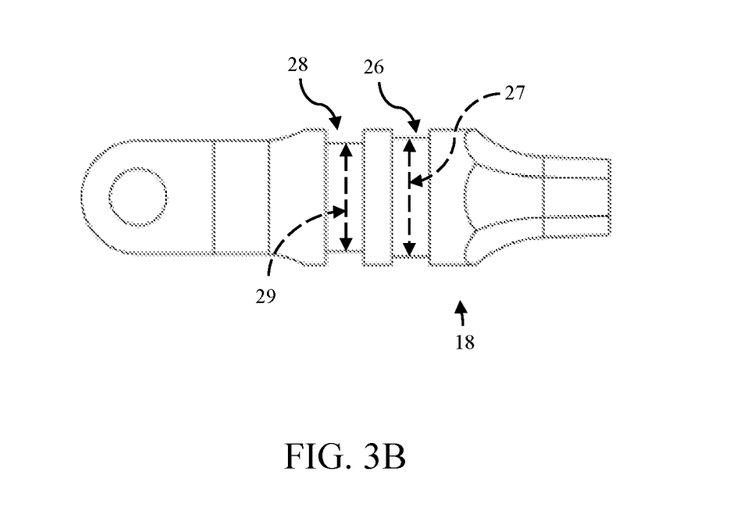
FIG. 3B shows a second side view of the driving bit of FIG. 2.

Referring to FIG. 3A, the shaft engaging portion 22 is disposed at the first end 30 and is configured to couple the driving bit 18 to the shaft 16. The shaft engaging portion 22 can couple the driving bit 18 to the shaft 16 in any appropriate manner. For example, in one embodiment, as shown in FIG. 1, a universal joint 39 couples the shaft 16 and the driving bit 18. In one such embodiment, as shown in FIGS. 2, 3A, and 3B, the shaft engaging portion 22 is a u-shaped extension that forms a portion of the universal joint 39.

Figure 3C:
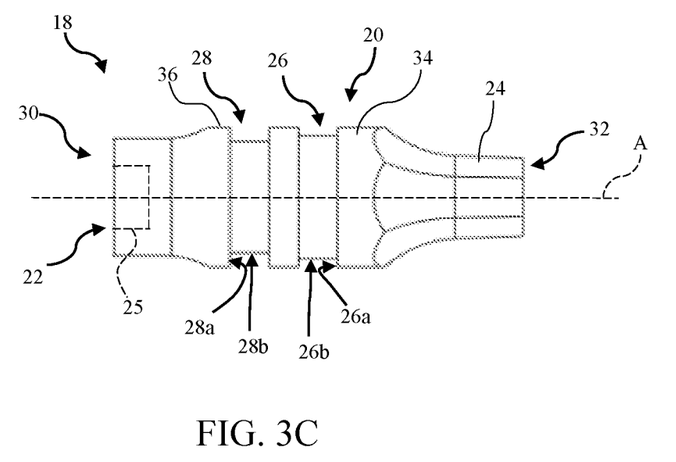
FIG. 3C shows a side view of a driving bit according to another embodiment of the present disclosure.

In another embodiment, as shown in FIG. 3C, the shaft engaging portion 22 forms an extension which is inserted into a recess in the universal joint 39. In an alternative embodiment, the shaft engaging portion 22 of the driving bit 18 includes a recess 25 configured to receive an extension of the universal joint 39, similar to a socket wrench. The driving bit 18 is, thereby, removably coupled to the shaft 16. In another alternative embodiment, the driving bit 18 is fixedly coupled to the shaft 16. For example, the driving bit 18 can be integrally formed with the universal joint 39.

The screw engaging portion 24 of the screw driving bit 18 is configured to engage a head of a screw. For example, as shown in FIGS. 2 and 3A, the screw engaging portion 24 can be in the form of a male head configured to engage a recess formed in the head of the screw. For example, the male head can have a hexagonal cross-section, similar to an Allen wrench, and be configured to mate with a hex socket of the head of the screw. The male head can also be in the form of a Torx head, a Torx plus head, a Phillips head, a bladed head, a Pozidriv head, a Supadriv head, a square head, or any other appropriate configuration. Alternatively, the screw engaging portion 24 can be in the form of a female head configured to engage a male head of the screw. The female head, for example, can be in the form of a hex socket.

The first circumferential groove 26 has side walls 26a and a bottom surface 26b. The side walls 26a can be oriented orthogonal to the longitudinal axis A such that the first circumferential groove 26 has a rectangular cross-section. Alternatively, the side walls 26a can be oriented at an oblique angle with respect to the longitudinal axis A. Orienting the side walls 26a at an oblique angle can allow a "lead-in" to the first circumferential groove 26 and allow easier engagement with the guide clamp 14. The bottom surface 26b of the first circumferential groove 26 defines a first outer diameter 27 (shown in FIG. 3B).

The second circumferential groove 28 has side walls 28a and a bottom surface 28b. The side walls 26a can be oriented orthogonal to the longitudinal axis A such that the second circumferential groove 28 has a rectangular cross-section. Alternatively, the side walls 28a can be oriented at an oblique angle with respect to the longitudinal axis A. Orienting the side walls 28a at an oblique angle can allow a "lead-in" to the second circumferential groove 28 and allow easier engagement with the guide clamp 14. The bottom surface 28b of the second circumferential groove 28 defines a second outer diameter 29 (shown in FIG. 3B).

As shown best in FIG. 3B, the second circumferential groove 28 is deeper than the first circumferential groove 26 such that the second outer diameter 29 is smaller than the first outer diameter 27. This allows the guide clamp 14 to restrict rotation of the driving bit 18 when engaged with the first circumferential groove 26 and allow rotation of the driving bit 18 when engaged with the second circumferential groove 28, as will be described in more detail herein.

The first circumferential groove 26 and the second circumferential groove 28 are offset from one another along the longitudinal axis A. In one embodiment, as shown in FIGS. 2, 3A, and 3B, the first circumferential groove 26 is distally disposed (i.e., closer to the screw engaging portion 24) relative to the second circumferential groove 28. Alternatively, in other embodiments, the first circumferential groove 26 is proximally disposed (i.e., closer to the shaft engaging portion 22) relative to the second circumferential groove 28.

In one embodiment, the first circumferential groove 26 and the second circumferential groove 28 circumscribe the entire circumference of the driving bit 18. In another embodiment, one or both of the grooves 26, 28 only circumscribe a portion of the driving bit 18. In one embodiment, the first circumferential groove 26 is a partial groove such that the guide clamp 14 can only engage and disengage the first circumferential groove 26 in certain orientations.

Figure 4A:
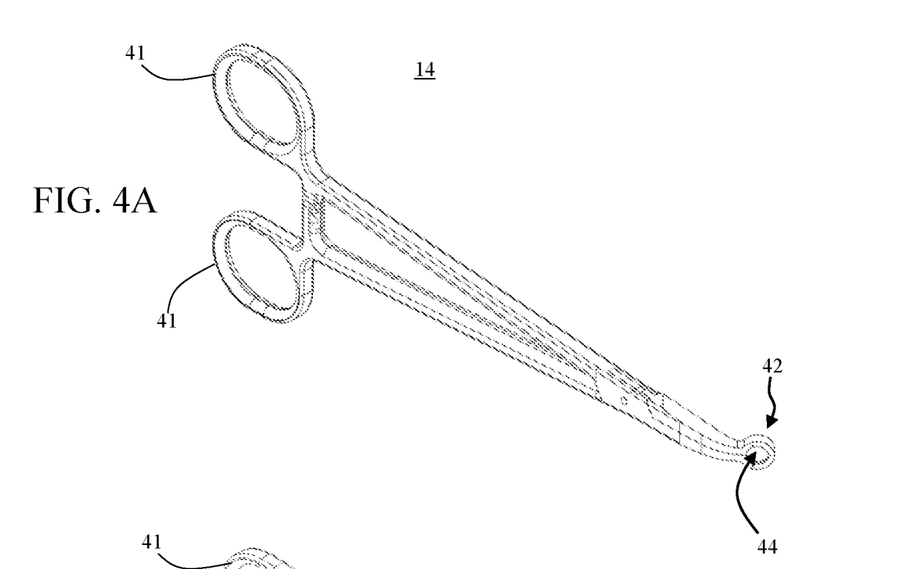
FIG. 4A shows a perspective view of a guide clamp in a closed configuration.
Figure 4B:
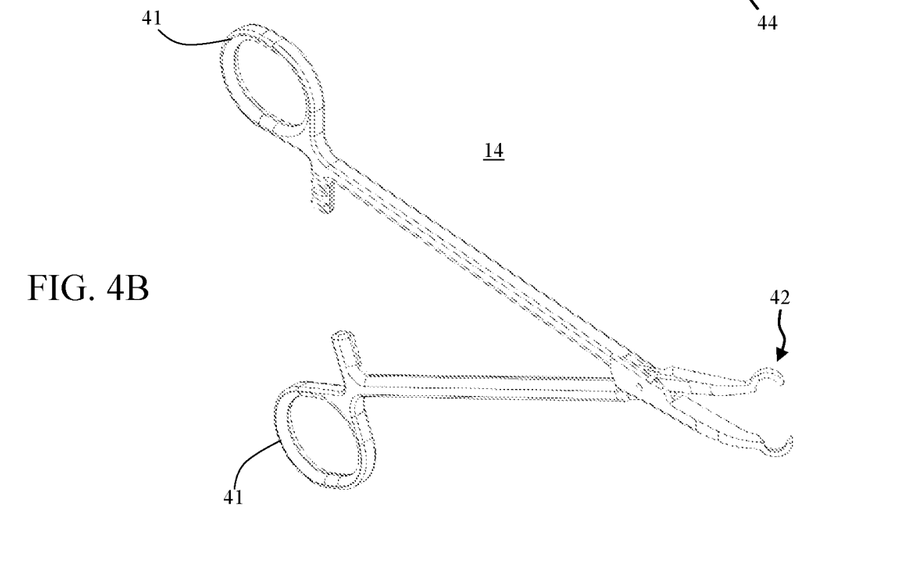
FIG. 4B shows a perspective view of the guide clamp in an open configuration.

As shown in FIGS. 4A and 4B, the guide clamp 14 includes arms 41 and a closable jaw 42. The closable jaw 42 forms an opening 44 when closed (shown in FIG. 4A), the opening 44 having a diameter that is smaller than the first outer diameter 27. As a result, the guide clamp 14 can tightly hold the driving bit 18 by engaging the closable jaw 42 into the first circumferential groove 26 and clamping the bottom surface 26b of the first circumferential groove 26. When engaged with the first circumferential groove 26, the guide clamp 14 prevents rotation of the driving bit 18. With the guide clamp 14 engaged with the first circumferential groove 26, the user is able to guide the driving bit 18 toward the head of the screw and engage the driving bit 18 with the head of the screw. The guide clamp 14 prevents rotation of the driving bit 18 to allow the driving bit 18 to be easily positioned in the desired orientation.

The opening 44 defined by the closable jaw 42 can be a circular opening or a semi-circular opening. For example, the opening 44 can enclose only a portion of the circumference of the driving bit 18, allowing the guide clamp 14 to be translated axially transverse to the longitudinal axis A to engage the grooves 26, 28.

In addition, the closable jaw 42 of the guide clamp 14 can rotatably hold the driving bit 18 by engaging the closable jaw 42 into the second circumferential groove 28. The diameter of the opening 44 is greater than the second outer diameter 29. As a result, the driving bit 18 is able to freely rotate about its longitudinal axis A while being held by the guide clamp 14. Alternatively, the diameter of the opening 44 is equal to or slightly less than the second outer diameter 29, but configured to grip the second circumferential groove 28 lightly such that the driving bit 18 is able to rotate. With the guide clamp 14 engaged with the second circumferential groove 28, the user is able to rotate the shaft 16 and, thereby, the driving bit 18 to tighten or loosen a screw. The engagement of the guide clamp 14 with the second circumferential groove 28 aids the user in manipulating the driving bit 18 and maintaining engagement of the driving bit 18 with the head of the screw.

Figure 5:
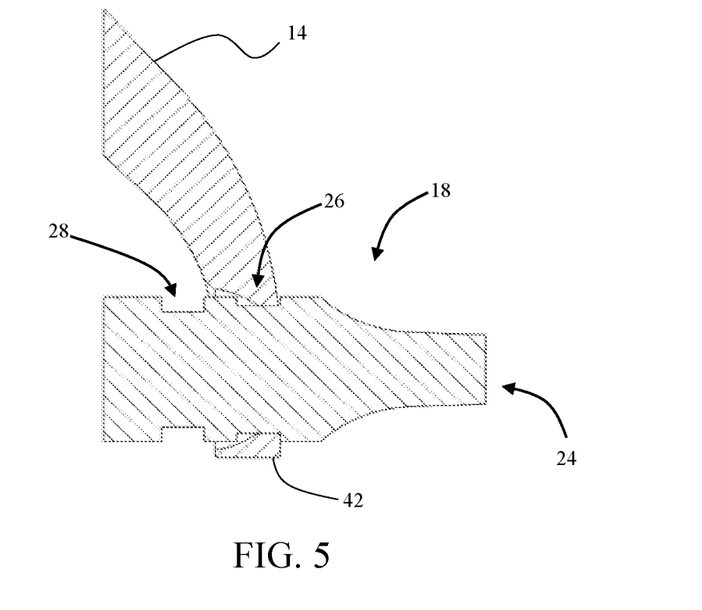
FIG. 5 shows a longitudinal cross-section view of the screw driver system of FIG. 1 in a first configuration in which a guide clamp is engaged with a first circumferential groove of the driving bit.
Figure 6:
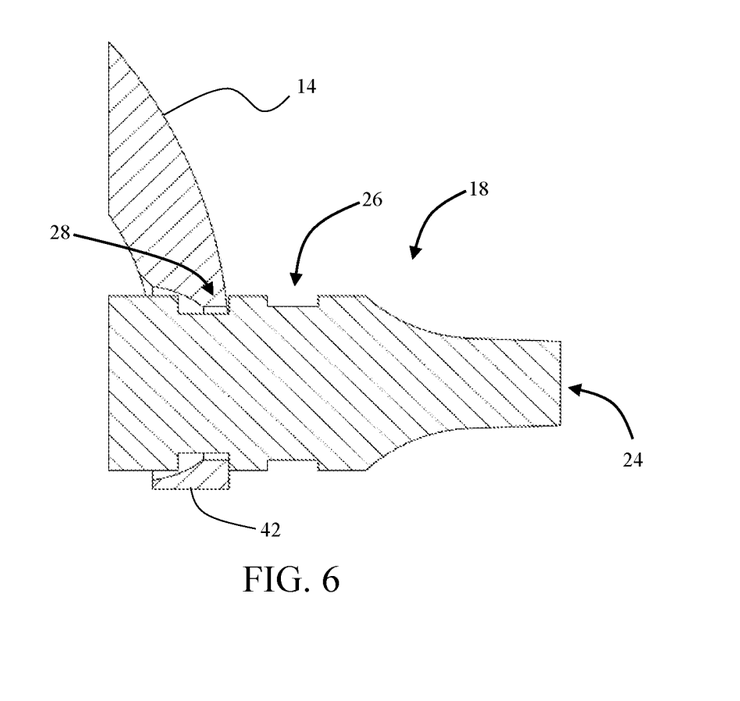
FIG. 6 shows a longitudinal cross-section view of the screw driver system of FIG. 1 in a second configuration in which the guide clamp is engaged with a second circumferential groove of the driving bit.

In use, the guide clamp 14 is initially engaged with the first circumferential groove 26 to prevent rotation of the driving bit 18, as shown in FIG. 5. After the screw engaging portion 24 of the driving bit 18 is engaged with the head of the screw, the closable jaw 42 is disengaged from the first circumferential groove 26. The closable jaw 42 is then moved to a position aligned with the second circumferential groove 28 and then closed to engage the second circumferential groove 28, as shown in FIG. 6. The user is then able to rotate the shaft 16 and driving bit 18 to tighten the screw while at the same time maintaining the guide clamp 14 in position to prevent the screw engaging portion 24 from disengaging the head of the screw.

The guide clamp 14 can be any instrument that can engage the first circumferential groove 26 and the second circumferential groove 28. For example, the guide clamp 14 can be forceps, as shown in FIGS. 4A and 4B. In one embodiment, squeezing the arms 41 of the forceps causes the closable jaw 42 to close and, thereby, engage the driving bit 18. The arms 41 can then be released to open the closable jaw 42 and disengage the driving bit 18.

Figure 7:
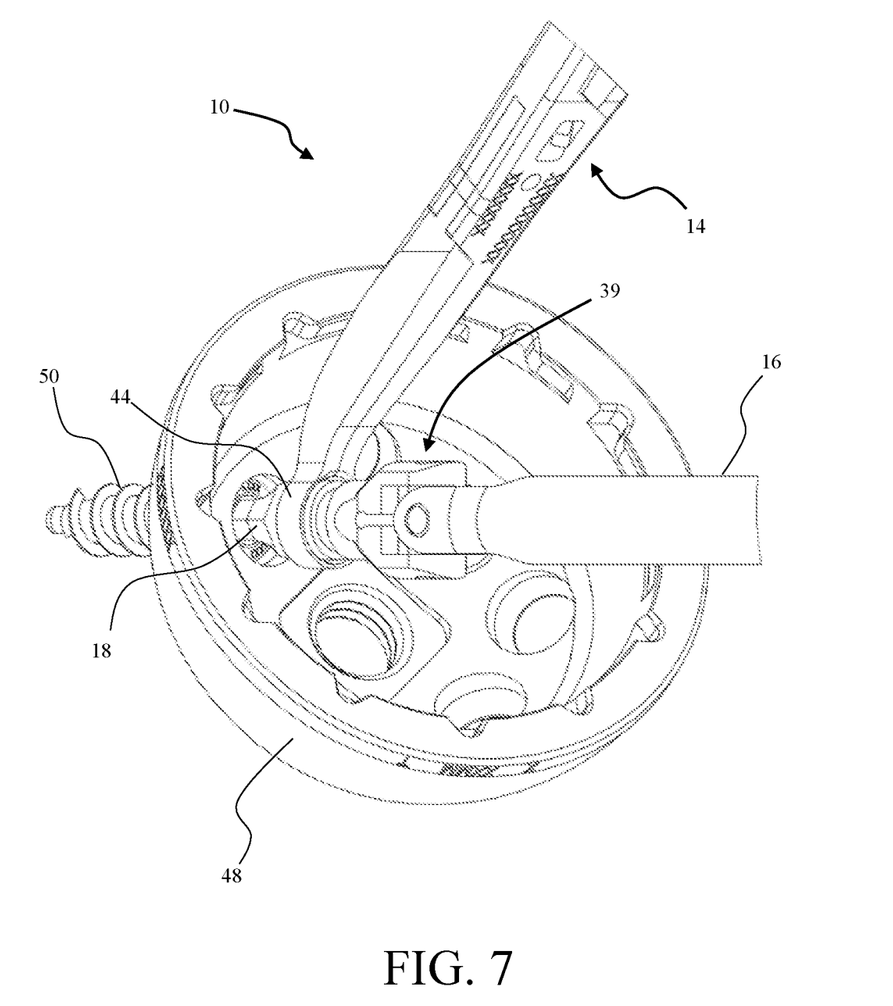
FIG. 7 shows a perspective view of the screw driver system of FIG. 1 engaged with a screw in an acetabular cup.

FIG. 7 is an illustration of the screw driver system 10 being used to secure an acetabular cup 48 to a patient's anatomy using one or more screws 50. In such a use, space constraints can limit a user's ability to manipulate a driving bit directly with their hand. This can make it difficult to accurately engage the driving bit with the screw. By providing a screw driver system 10 of the screw driving bit 18 and the guide clamp 14 that are configured to cooperate in the manner described above, the user can easily guide the screw driving bit 18 onto a screw 50 and tighten or unscrew the screw 50.

According to another aspect, a method for using the screw driving bit 18 for tightening or loosening a bone screw is disclosed. The method comprises: tightly holding the screw driving bit with a guide clamp 14 by engaging the first circumferential groove's bottom surface with the guide clamp; guiding the screw engaging portion of the screw driving bit onto the head of the bone screw; releasing the guide clamp from the first circumferential groove; rotatably holding the screw driving bit with the guide clamp by engaging the second circumferential groove's bottom surface with the guide clamp; and tightening or loosening the bone screw by turning the screw driving bit while rotatably holding the screw driving bit with the guide clamp.

Figure 8:
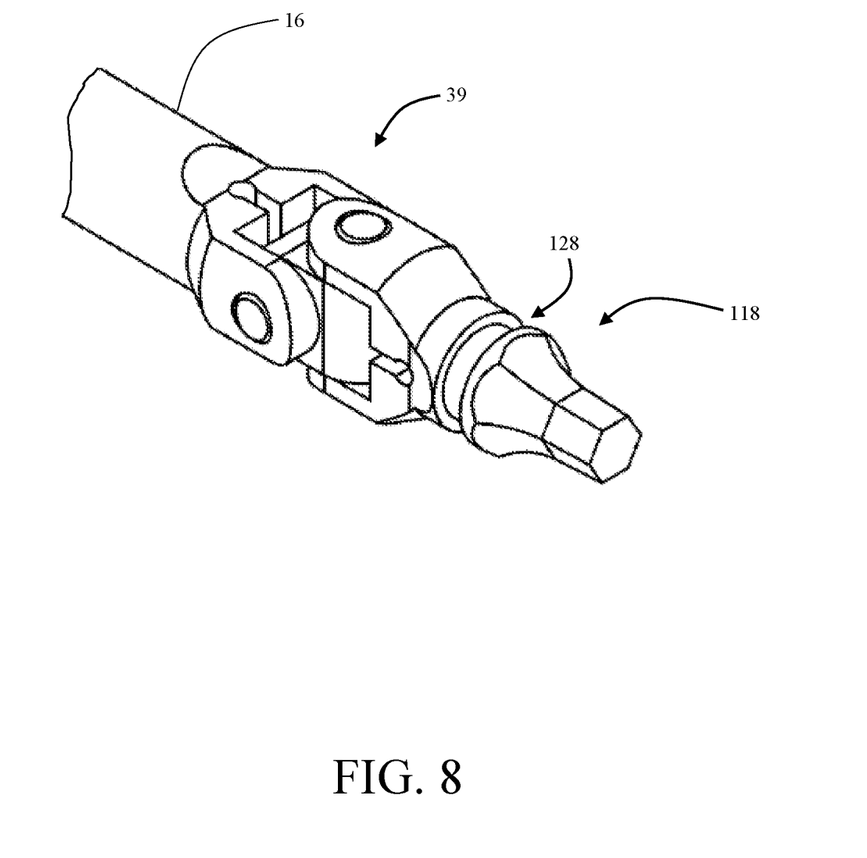
FIG. 8 shows a perspective view of a driving bit according to another embodiment of the present disclosure.

In another embodiment, as shown in FIG. 8, a screw driving bit 118 is provided where the screw driving bit 118 has just one circumferential groove 128 that is a free spinning groove like the second circumferential groove 28 provided on the screw driving bit 18. Thus, the screw driving bit 118 is utilized in situations where there is no need to fixedly hold the screw driving bit with the guide clamp. The guide clamp is just used to guide the screw driving bit 118 onto a screw then hold the screw driving bit 118 while the screw is tightened.

According to another aspect, a method for using the screw driving bit 118 for tightening or loosening a bone screw is disclosed. The method comprises: rotatably holding the screw driving bit 118 having the single circumferential groove 128 with a guide clamp 14 by engaging the circumferential groove's bottom surface with the guide clamp; guiding the screw engaging portion of the screw driving bit onto the head of the bone screw; and tightening or loosening the bone screw by turning the screw driving bit while rotatably holding the screw driving bit with the guide clamp.

In another embodiment, a method of installing a screw in an acetabular cup using the screw driver systems described herein is provided. The method includes providing a screw driver system including a screw driver and a guide clamp. The screw driver system includes a driving bit having a first circumferential groove and a second circumferential groove. The method further includes engaging the guide clamp with the first circumferential groove such that the guide clamp restricts rotation of the driving bit. The method further includes engaging a screw engaging portion of the driving bit with a head of the screw. The method also includes disengaging the guide clamp from the first circumferential groove and engaging the guide clamp with the driving bit's second circumferential groove such that the driving bit is able to rotate with respect to the guide clamp. The method also includes rotating the driving bit to install the screw.

In another embodiment, a method of removing a screw from an acetabular cup using the screw driver systems described herein is provided. The method includes providing a screw driver system including a screw driver and a guide clamp. The screw driver system includes a driving bit having a first circumferential groove and a second circumferential groove. The method further includes engaging the guide clamp with the first circumferential groove such that the guide clamp restricts rotation of the driving bit. The method further includes engaging a screw engaging portion of the driving bit with a head of the screw. The method also includes disengaging the guide clamp from the first circumferential groove and engaging the guide clamp with the driving bit's second circumferential groove such that the driving bit is able to rotate with respect to the guide clamp. The method also includes rotating the driving bit to remove the screw.

While the foregoing description and drawings represent preferred or exemplary embodiments of the present invention, it will be understood that various additions, modifications and substitutions may be made therein without departing from the spirit and scope and range of equivalents of the accompanying claims. In particular, it will be clear to those skilled in the art that the present invention may be embodied in other forms, structures, arrangements, proportions, sizes, and with other elements, materials, and components, without departing from the spirit or essential characteristics thereof. In addition, numerous variations in the methods/processes described herein may be made without departing from the spirit of the invention. One skilled in the art will further appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims and equivalents thereof, and not limited to the foregoing description or embodiments. Rather, the appended claims should be construed broadly, to include other variants and embodiments of the invention, which may be made by those skilled in the art without departing from the scope and range of equivalents of the invention. All patents and published patent applications identified herein are incorporated herein by reference in their entireties.

What is claimed is:

1. A screw driver system comprising:
a screw driving bit comprising:
  a unitary body having a first end and a second end and defining a longitudinal axis between the first end and the second end, wherein the body having an outer surface between the first end and the second end;
  a shaft engaging portion at the first end configured to couple to the shaft;
  a screw engaging portion at the second end, the screw engaging portion shaped and configured to engage a head of a screw; and
  a first circumferential groove and a second circumferential groove provided on the outer surface of the body,
    wherein each of the circumferential grooves having side walls and a bottom surface,
    wherein the bottom surface of the first circumferential groove defining a first outer diameter and the bottom surface of the second circumferential groove defining a second outer diameter,
    wherein the second circumferential groove is deeper than the first circumferential groove, whereby the second outer diameter is smaller than the first outer diameter; and
a guide clamp comprising:
  at least one arm;
  a closable jaw for holding the screw driving bit, wherein the jaw forms an opening when closed, wherein the opening having a diameter that is larger than the second outer diameter of the screw driving bit but smaller than the first outer diameter of the screw driving bit,
  whereby the guide clamp can tightly hold the screw driving bit by engaging the closable jaw into the first circumferential groove and clamping the first circumferential groove's bottom surface and restricting the screw driving bit from rotating about a longitudinal axis of the screw driving bit; and
  whereby the guide clamp can rotatably hold the screw driving bit by engaging the closable jaw into the second circumferential groove without clamping the second circumferential groove's bottom surface, thus allowing the screw driving bit to rotate about the longitudinal axis of the screw driving bit while being held by the guide clamp.

2. The screw driver system of claim 1, wherein the first circumferential groove and the second circumferential groove are fixed in an arrangment wherein they are coaxially positioned about the longitudinal axis.

3. The screw driver system of claim 1, wherein the screw engaging portion includes a male portion configured to engage a socket head screw.

4. The screw driver system of claim 1, the screw engaging portion includes a recess configured to receive a male head screw.

5. The screw driver system of claim 1, wherein the first circumferential groove is distal to the second circumferential groove.

6. The screw driver system of claim 1, wherein each of the circumferential grooves has a rectangular cross sectional shape.

7. The screw driver system of claim 1, wherein the second circumferential groove is distal to the first circumferential groove.

* * * * *